United States Patent
Dray

Patent Number: 5,921,949
Date of Patent: Jul. 13, 1999

[54] CARPAL TUNNEL WRIST CORRECTIVE SUPPORT

[76] Inventor: James A. Dray, 3320 Clinton Parkway Ct., #200, Lawrence, Kans. 66047-2650

[21] Appl. No.: 08/884,877

[22] Filed: Jun. 30, 1997

Related U.S. Application Data

[63] Continuation-in-part of application No. 08/600,237, Feb. 12, 1996., abandoned

[51] Int. Cl.$^6$ .............................. A61F 13/00; A41D 19/00
[52] U.S. Cl. .................................. 602/64; 602/21; 2/162; 2/170
[58] Field of Search .................................. 602/20, 21, 60, 602/64, 69; 128/877–881; 2/162, 170

[56] References Cited

U.S. PATENT DOCUMENTS

| | | |
|---|---|---|
| 4,048,991 | 9/1977 | Marx . |
| 4,831,997 | 5/1989 | Greene . |
| 4,832,010 | 5/1989 | Lerman . |
| 4,966,137 | 10/1990 | Davini . |
| 4,991,234 | 2/1991 | Greenberg . |
| 5,350,418 | 9/1994 | Janevski et al. ........................ 602/21 |
| 5,441,058 | 8/1995 | Fareed . |
| 5,466,215 | 11/1995 | Lair et al. . |
| 5,468,220 | 11/1995 | Sucher . |
| 5,478,306 | 12/1995 | Stoner . |

FOREIGN PATENT DOCUMENTS

| | | | |
|---|---|---|---|
| 3838564 | 5/1990 | Germany | ................................. 602/64 |

*Primary Examiner*—Richard J. Apley
*Assistant Examiner*—Kim M. Lee
*Attorney, Agent, or Firm*—Chase & Yakimo, L.C.

[57] ABSTRACT

An orthosis for external application to the wrist for treatment of carpal tunnel syndrome, which applies simultaneous yet independent bilateral parallel midline compression along with simultaneous yet independent anterior midline torsion to the distal ends of the radius and ulna and the lateral and medial wall of the carpal bones. The orthoses relaxes the flexor retinaculum (transverse and volar carpal ligaments), reverses anterior to posterior prolapse of the carpal tunnel, and reduces stress on the median nerve, ligaments and bursa traversing the wrist. The device is constructed to allow full and unrestricted movement of the wrist, hand and fingers. The device utilizes a flexible substrate to which are attached releasable compression elements for positioning at the distal end of the radius and ulna at the lateral walls of the carpal tunnel. A cinching loop and a releasable closure element are integrally constructed into the substrate material for securing the device to the wrist such that the compression and torsion act on the elements which are transferred to the radius and ulna ends. The device is constructed so as to be worn on either the right or left wrist and accommodates either large or small wrist circumferences.

16 Claims, 5 Drawing Sheets

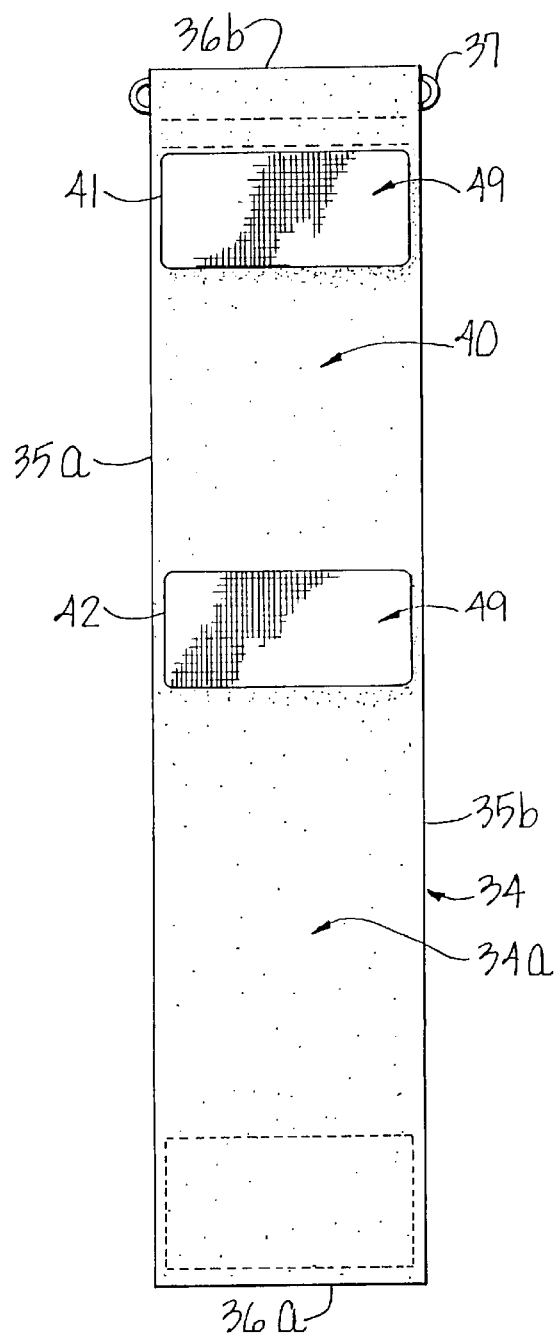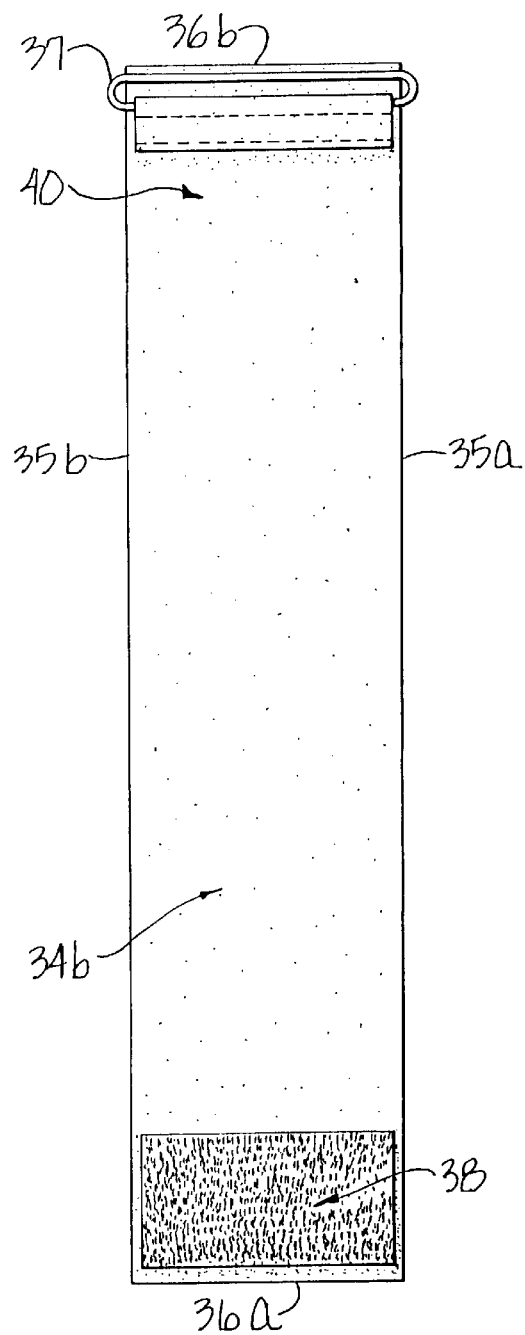

CARPAL TUNNEL WRIST CORRECTIVE SUPPORT

CROSS REFERENCE TO RELATED APPLICATION

This application is a continuation in part of application Ser. No. 08/600,237, filed Feb. 12, 1996, now abandoned.

BACKGROUND OF THE INVENTION

FIELD OF THE INVENTION

The present invention relates generally to orthopedic supports for the wrist and to the management and treatment of wrist sprain, carpal tunnel syndrome and tendinitis of the wrist and forearm and hand. More specifically the present invention represents a new and innovative approach to carpal tunnel problems. The present invention simultaneously applies independent anterior midline compression and anterior midline torsion to the distal ends of the radius, ulna and lateral walls of the carpal bones, to relax the flexor retinaculum (the transverse and volar carpal ligaments) and reverse posterior to anterior (dorsal to palmer) prolapse of the carpal tunnel. In so doing, this device relieves pressure on the median nerve, carpal ligaments and other soft tissue structures of the wrist while allowing full and unrestricted motion of the wrist, hand and fingers.

"Carpal Tunnel Syndrome", as well as many cases of tendinitis and other cumulative trauma disorders (CTD's) of the wrist and forearm, result from repeated trauma to the tendons and soft tissue structures that pass through the wrist. Excessive pressure on the carpal tunnel contents, including the flexor tendons and bursa, results in abnormal function, weakness, inflammation, pain, numbness and ultimately in injury to the median nerve.

The carpal tunnel is composed of a bony arch formed by the radius, ulna and carpal bones and closed by the flexor retinaculum which anchors the base of the arch together.

The flexor retinaculum is a thick, unyielding ligamentous band that crosses the groove on the palmer surface of the carpal bones. It is composed of the palmer (volar) carpal ligament and transverse (anterior annular) carpal ligament. The palmer carpal ligament is attached medially and laterally to the styloid processes of the radius and ulna. The transverse carpal ligament is attached medially to the pisiform bone and the hamulus of the hamate, and laterally to the tuberosity of the scaphoid and palmer surface of the ridge of the greater multangular (trapezium). The fibers of these ligaments merge at the distal end of palmer and proximal end of the transverse ligament. Together with the carpal bones, they form a tunnel through which pass the deep flexor tendons and median nerve.

The median nerve lies in the carpal tunnel adjacent the flexor retinaculum and between it and the flexor tendons and their bursa. The carpal tunnel is barely adequate to accommodate these structures and it is generally felt that any narrowing of the diameter of the tunnel or decrease in the diameter to contents ratio, causes injury to the median nerve by repeatedly pressing it against the relatively unyieldable retinaculum. Repetitive forceful movement, in particular extension movements of the hand, are thought to repeatedly traumatize the median nerve in this manner.

A study of FIGS. 1–3 reveals that prolapse or collapse which narrows the tunnel in such a way as to compress the internal structures against the flexor retinaculum, occurs primarily in posterior (dorsal) to anterior (palmer) direction. Posterior to anterior displacement would result in decreasing the posterior to anterior diameter of the tunnel, makes the flexor retinaculum more taut and compresses the flexor tendons and median nerve against the taut retinaculum. Midline movement of the bony structures or anterior to posterior movement of the carpals would have the opposite effect however, i.e., relaxing the flexor retinaculum and increasing the posterior to anterior diameter of the tunnel.

Current medical treatment of carpal tunnel syndrome consists of rest, restriction from traumatizing activities, limiting movement with restrictive splints, anti-inflammatory medication and cortisone injections. In advanced cases surgery is used to transect and spread the transverse carpal ligament to allow more room for the contents of the carpal tunnel, i.e., an increase in the diameter to contents ratio. Some form of wrist support or splint is normally used in the early stages of treatment. They are used in an attempt to delay progression of the condition or as an adjunct to some other treatment in an effort to lessen the pain and aid in the return to normal function. Subsequent to surgery, wrist splints are frequently used to support the wrist and aid in recovery. Thus it is important that a presurgical device be provided which corrects the condition or prevents further development and/or progression of the condition.

Many types of orthoses, referred to as braces, supports and splinting devices, have been proposed to address this problem, e.g., shown in Des. Pat. No. 339,866 and U.S. Pat. No. 4,883,073. Such supports typically include metal or some type of reinforcing part to restrict or limit movement, e.g., shown in U.S. Pat. Nos. 4,047,250, 4,883,073 and 5,267,943. These devices usually include a part that fits around the thumb and hand such as a thumb loop, or some other means of securing the device to the arm and hand to prevent slippage.

Devices like those referenced above, either partially or totally limit or inhibit flexion and/or extension movements of the wrist and abduction and adduction movements are also inhibited. Dexterity of the hand, wrist and fingers is also generally compromised. In theory, these supports limit the stress by limiting the movement.

U.S. Pat. Nos. 4,628,918 and 5,372,575, represent yet another type of orthosis which is intended to compress musculoskeletal structures to achieve a therapeutic effect. U.S. Pat. Nos. 4,048,991, uses circumferential compression in an attempt to lock the wrist and carpal bones in a so called neutral position. U.S. Pat. No. 4,966,137, utilizes straight line compression to squeeze the distal forearm, i.e. the radius and ulna in an attempt to alter the carpal tunnel. Still other types of compressive devices, such as U.S. Pat. Nos. 4,991, 234 and 5,478,306, represent simple devices which have long been used for general support. Still another type of device represented by U.S. Pat. Nos. 5,468,220 and 5,256, 136, attempts to stretch the flexor retinaculum.

The above referenced devices fail to account for the dynamics of bone and joint movement and the structural dynamics of the carpal tunnel. Forces applied to the carpal area of the wrist must be directed at relaxing the flexor retinaculum and increasing the anterior to posterior diameter of the carpal tunnel, i.e. reversing posterior to anterior prolapse. These actions allow more unrestricted room for the contents of the carpal tunnel.

Bones and joints are known to generally resist compressive forces. By contrast torsional forces are known to move bones and joints to the point that, if excessive, will injure the joint and supporting tissues. Therefore a simple compression of the bones and joints of the wrist, whether straight line or circumferential, would be resisted and would not significantly alter the posterior to anterior prolapse of the carpal bones or relax the flexor retinaculum. To achieve such conditions the device should provide compressive forces on both sides of the carpal tunnel along with anterior midline torsion forces thereon so that each side of the carpal tunnel is simultaneously compressed and torsioned toward the anterior midline. Such forces must be in excess of any forces acting on the dorsal side of the tunnel so as to increase the diameter of the carpal tunnel in an anterior to posterior direction and reverse prolapse.

Thus, a device which relaxes the flexor retinaculum and reverses carpal prolapse would provide maximum benefits. The above referenced devices do not simultaneously apply bilateral anterior midline compression forces along with anterior midline torsional forces on the carpal tunnel, these forces necessary to alter the bony and soft tissue structures of the wrist. Thus, the desired actions on the carpal tunnel are not performed.

Current methods of treatment alone or in combination have met with varying degrees of success. Current methods of splinting or supporting the wrist, which are widely used in early cases, are inadequate and fail to significantly alter the progression of the carpal problematic conditions. Even when "successfully" treated by current methods, carpal tunnel problems often return as soon as the patient returns to work or resumes the activities that precipitated the onset of symptoms. With carpal tunnel surgery the patient is frequently left with varying degrees of residual dysfunction, and a lifetime of continuing problems.

Carpal Tunnel Syndrome and its corollary conditions account for an increasing cost in terms of workers compensation claims, lost productivity and settlements. These conditions have now surpassed back injury as the No. 1 cause of workers compensation costs. Since wrist splints and supports are often the earliest form of treatment and prevention, it is imperative that a type of support be developed that insures a high probability of success, has preventative value, is inexpensive and simple to use without requiring costly doctors visits and fitting fees, and allows for quick return to normal and full function of the affected person.

SUMMARY OF THE INVENTION

One object of the current invention is to simultaneously deliver independent compressive and torsional forces to the bones of the wrist and forearm in such a way as to relax the flexor retinaculum of the carpal tunnel.

Another object of the current invention is to simultaneously deliver independent compressive and torsioning forces to the carpal bones so as to reverse posterior to anterior carpal tunnel prolapse.

Another object of this invention is to reverse the effects of stress from posterior to anterior prolapse of the carpal bones.

Yet another object of this invention is to accomplish the foregoing without limiting or inhibiting movement of the wrist, hand or fingers.

Still another object of this invention is to provide an easily applied device which is adaptable to either the right or left hand and to small or large circumference wrists without special modification.

A further object of this invention is to provide a device which is easily cleaned yet durable with a long potential for use and which can be worn for long periods of time without adverse effects.

Yet another intention of the current invention is to provide a device with the potential of application to other anatomical structures of similar construction to the wrist, such as the ankle, and which is potentially adaptable for other musculoskeletal compressive purposes.

Still another object of the current invention is to provide an inexpensive device which is simple to use and does not require a prescription or special fitting by a healthcare professional of special anatomical knowledge.

Other objects and advantages of this invention will become apparent from the following description taken in connection with the accompanying drawings, wherein is set forth by way of illustration and example, an embodiment of this invention.

The present invention simultaneously delivers independent anterior midline compression and anterior midline torsion to the radial and ulnar styloid processes and the lateral walls of the carpal tunnel to which the ligaments comprising the flexor retinaculum are attached. In compressing and torsioning these structures, the flexor retinaculum is relaxed and the dorsal (posterior) to palmer (anterior) carpal tunnel prolapse is minimized or reversed. Thus, the flexor retinaculum does not aggravate the adjacent flexor tendons and median nerves. Moreover, the reverse of the prolapse increases the diameter of the carpal tunnel to allow more room for the tunnel contents.

Unlike currently available supports, the present invention does not limit motion, which is in itself stressful on the joints and tendons causing disuse and functional problems. Rather, the device is constructed to allow full motion of the wrist, hand and fingers, placing virtually no pressure on the anterior (palmer) or posterior (dorsal) side of the wrist. Since the wrist is the narrowest point between the elbow and hand, the device will not slip toward the hand or up the forearm and requires no thumb loop to remain in place. Finger, hand and wrist dexterity is, therefore, not compromised.

No other support simultaneously combines independent midline compression with independent anterior midline torsioning of the radial and ulnar styloid processes and carpal bones while allowing full active range of motion while being worn. No other support reverses prolapse of the carpal tunnel or relaxes the flexor retinaculum by simultaneously compressing and torsioning the lateral walls of the carpal tunnel toward the anterior midline.

BRIEF DESCRIPTION OF THE DRAWINGS

FIG. 4 is a view of the inside surface of the preferred embodiment of the current invention.

FIG. 5 is a view of the outside surface of the preferred embodiment of the current invention.

DESCRIPTION OF THE PREFERRED EMBODIMENT

Figures 1, 2:
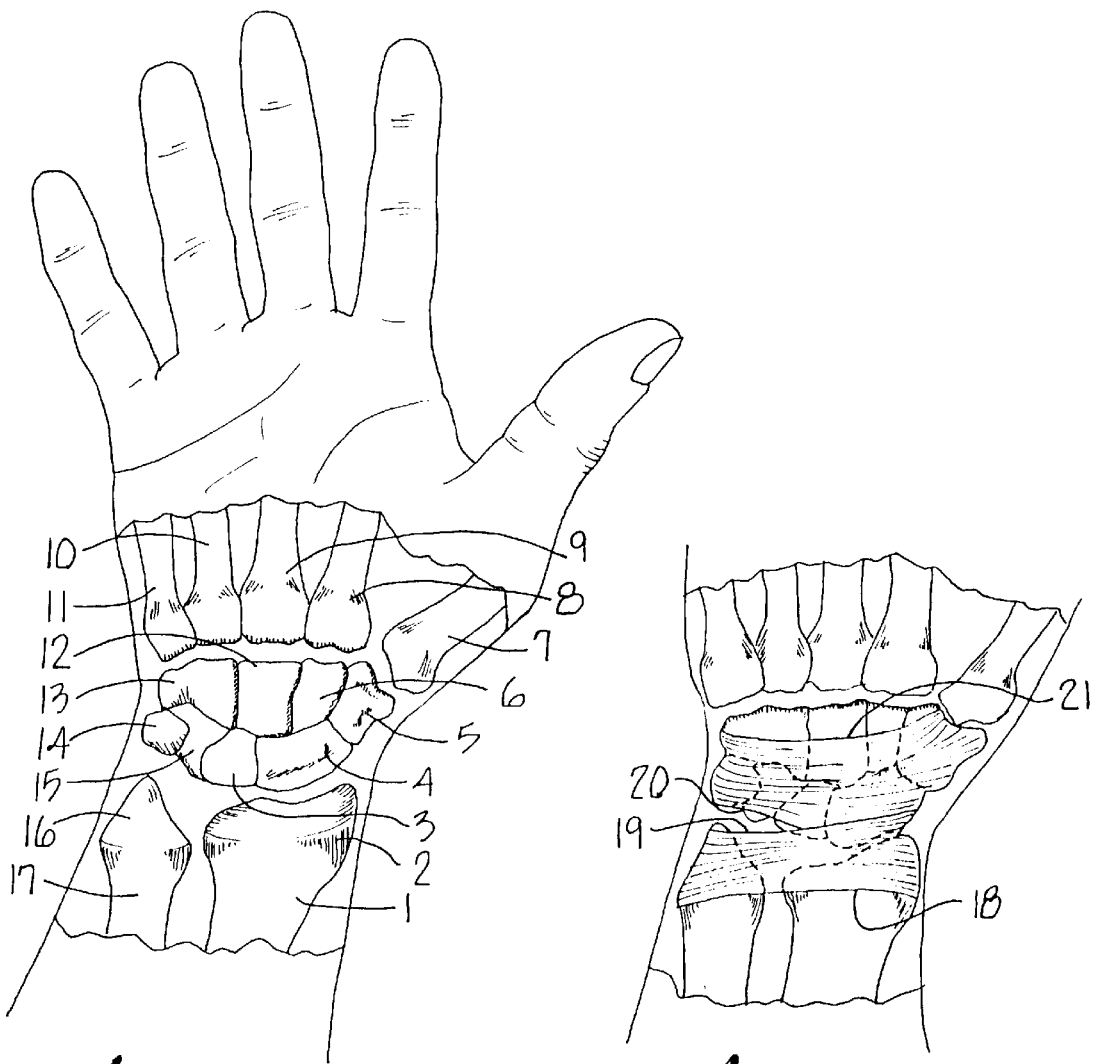
FIG. 1 is a palmer (anterior) view of the distal forearm of the right hand, showing the relationship of the bones of the wrist, carpal tunnel and metacarpals to each other.
FIG. 2 is a fragmentary palmer (anterior) view of the distal forearm and wrist of the right hand showing the flexor retinaculum (transverse and volar carpal ligaments) and its attachment to the bones of the forearm and wrist.
Figure 3:
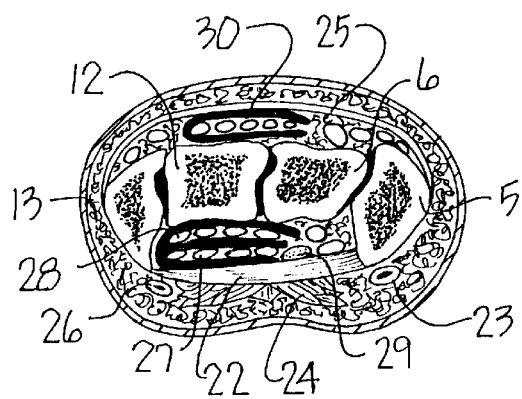
FIG. 3 is a transverse view through the carpal tunnel with the wrist in pronation (palm or anterior side down), showing the structure of the carpal tunnel and relationship of the flexor retinaculum and the deep flexor tendons and bursa to the median nerve as they pass through the prolapsed carpal tunnel.

Referring to FIG. 4, the depicted device includes a strap 34 shown in a flat open position with the inside surface 34, facing upward. The flexible strap 34 is rectangular in configuration presenting side edges 35a, 35b and ends 36a, 36b being clearly visible. Integrally sewn into one end 36b of the substrate material is a cinching loop 37, through which the opposite end 36a of the strap 34 is threaded creating a circumferential strap. The inner surfaces of the radial compression pad 41, and ulnar compression pad 42, are also depicted in FIG. 4. (Designation of the elements as radial and ulnar is for reference purposes only, as the compression elements 41, 42 are identical for both anatomical locations.) Referring to FIG. 5, the outside surface of the strap device is depicted. A closure device consisting of nylon hook material 38, is integrally sewn into the substrate material on the end 36a opposite the end 36b with the cinching loop 37.

Figure 6:
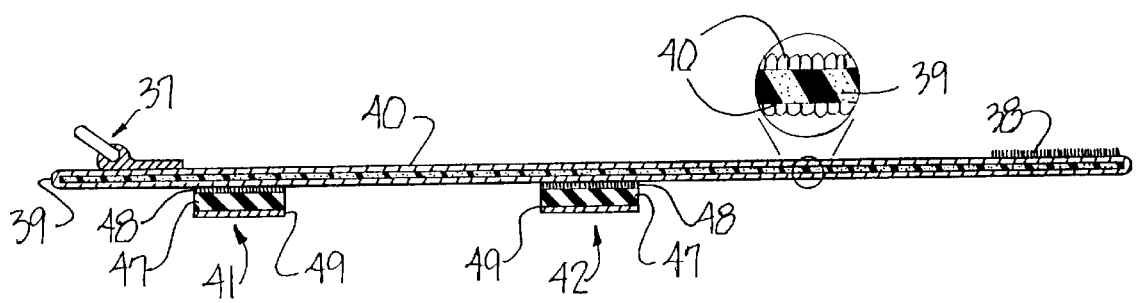
FIG. 6 is a side view of the preferred embodiment of the current invention.

Referring to FIG. 6, the flexible substrate 34 of the device is seen to be a laminate with a base or inner layer of neoprene rubber 39. Both the inside 34a and outside 34b surfaces are composed of a layer of unbroken loop fabric 40, to which the radial compression element 41, ulnar compression element 42 and the nylon hook closure material 38 are readily attached.

Figure 7:
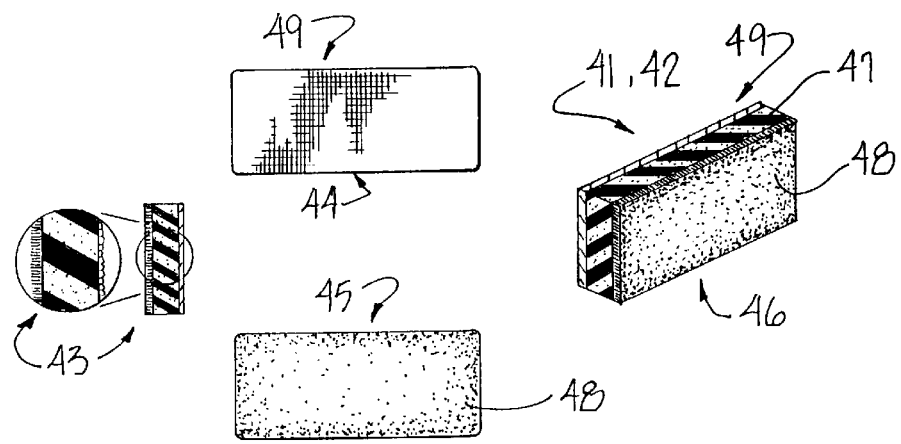
FIG. 7 are front, back, side and perspective views of the preferred embodiment of one of the compression elements.

Referring to FIG. 7, the compression element 41 or 42 is shown in end 43, inside surface 44, outside surface 45, and oblique views 46. Each compression element is seen to be a laminate consisting of a base or inner layer of neoprene rubber 39, which is dense yet pliable enough to conform to the contours and bony protuberances of the processes but prevents rotational or circumferential slippage of the device about the wrist when being worn. The laminate surface of the compression element consists of a hook material 48 which allows easy attachment to the unbroken loop material 40 on the inside surface 34a of the circumferential strap 34. The opposed, free laminate surface 49 of the compression element consists of a soft, smooth, material suitable for prolonged contact with the skin.

Figure 8:
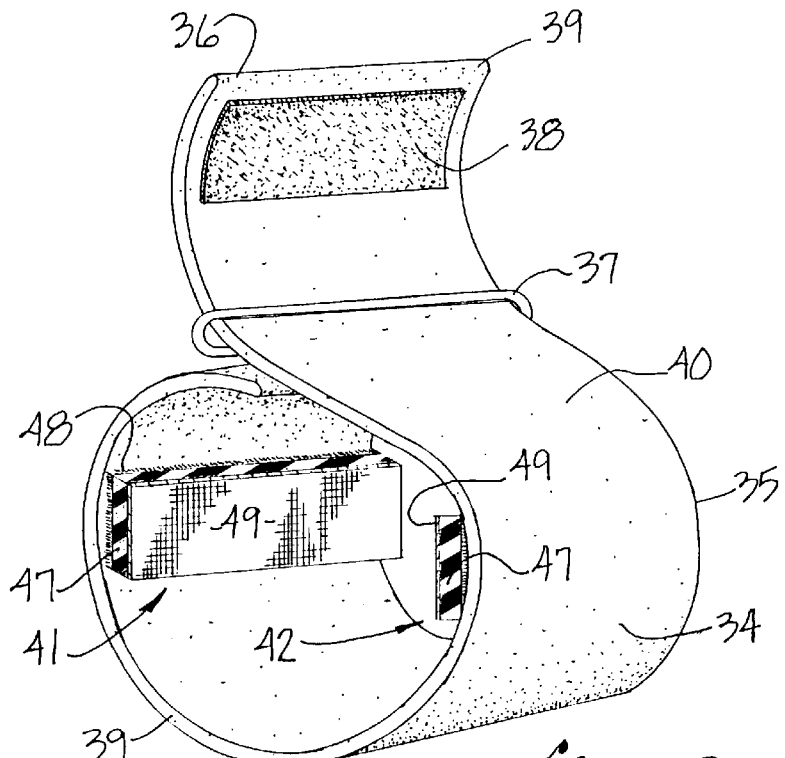
FIG. 8 is an oblique perspective of the preferred embodiment of the current invention.

Referring again to FIG. 8, the hook 48 and loop 40 composition of the components of the device allows the compression elements 41, 42 to be placed on the strap 34 surface 34a at varying distances apart so as to accommodate different wrist circumferences.

Figure 9:
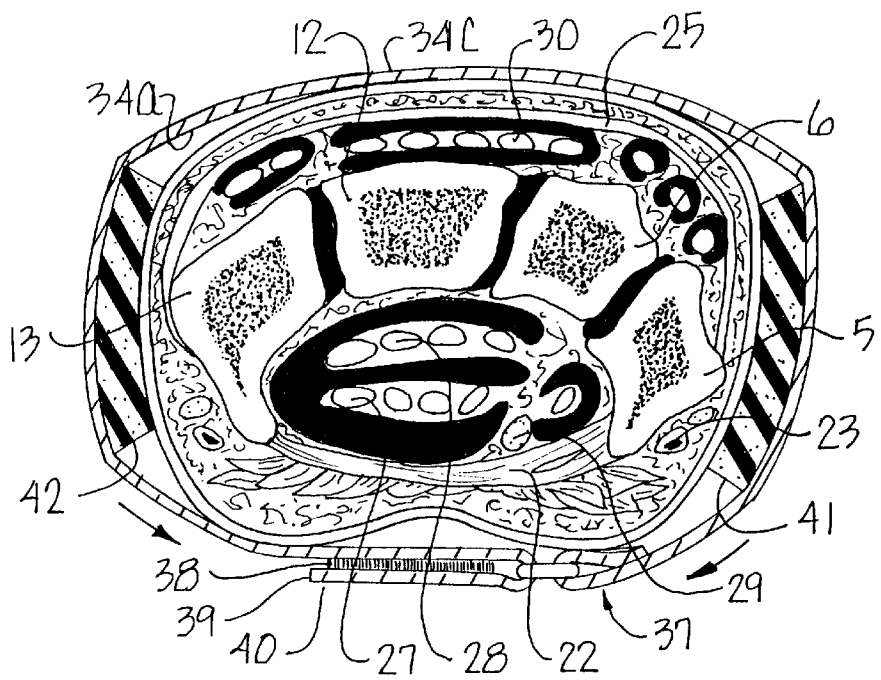
FIG. 9 is a transverse view of the carpal tunnel showing the relationship of the preferred embodiment of the present invention to the wrist and carpal structures with a preferred application of the support with the buckle on the palmer side of the wrist.
Figures 10, 11:
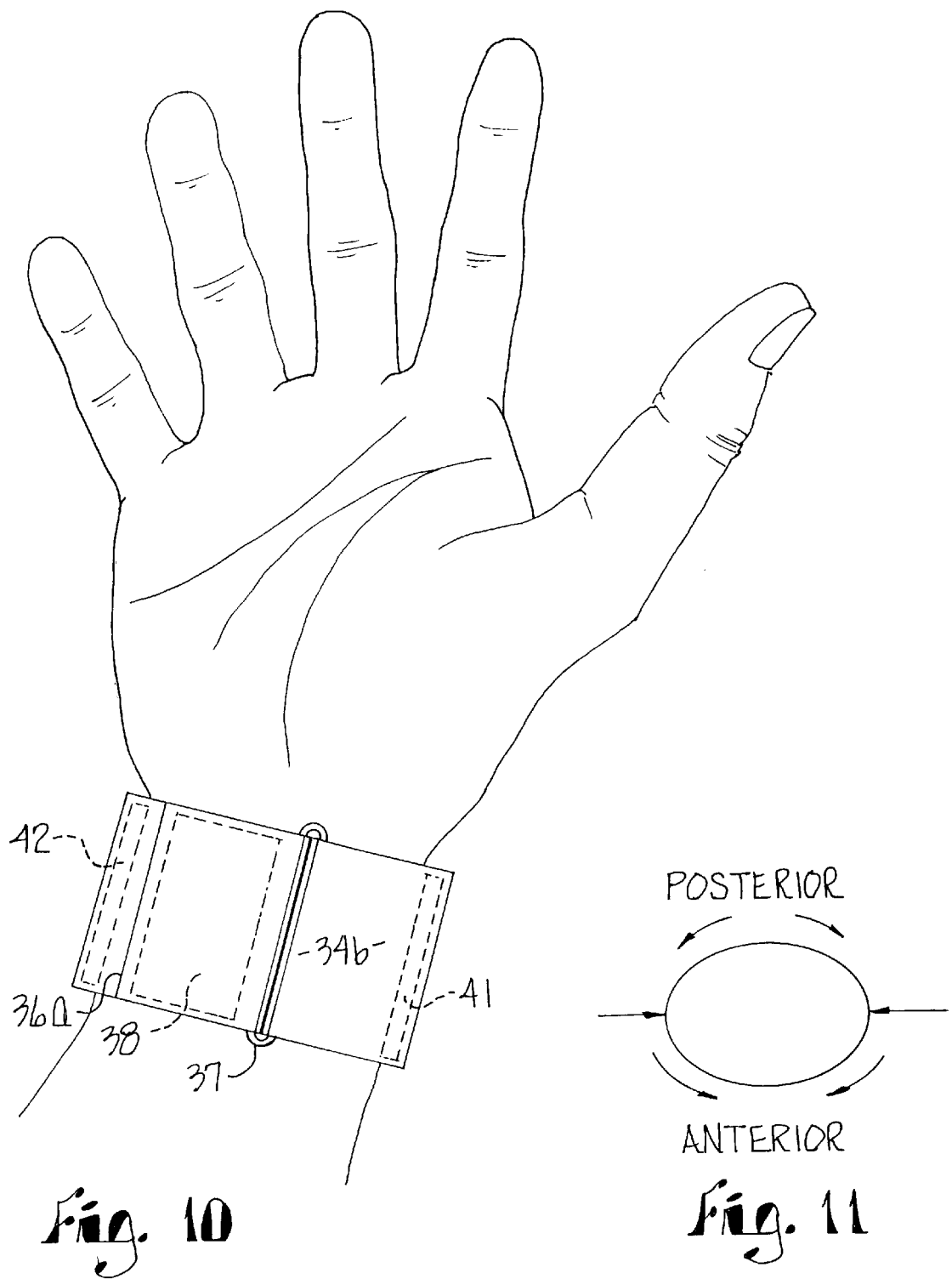
FIG. 10 is a palmer perspective of the distal forearm and wrist showing the relative relationship of the preferred embodiment of the current invention to the wrist and forearm when the device is properly positioned and closed with the buckle on the palmer side of the wrist.
FIG. 11 is a diagrammatic view of the forces presented on the carpal tunnel by the current invention.

Referring to FIG. 9, the device is depicted about the wrist with the anterior or palmer side of the wrist down. This FIG. 9 illustration shows the relative relationship of the compression elements 41, 42 about the wrist and adjacent the radius and styloid processes so as to cause the desired therapeutic compressive and torsioning forces thereon. As shown each compression element 41, 42 is first positioned adjacent the radius and styloid process of the ulna with the strap ends being on the anterior side of the wrist. Upon extension of end 36 through cinch 37 and fastening of the hook end material 38 to the loop 40 material, the strap will be secured to the wrist. Movement of the hook material 38 towards the dorsal portion 34c of the strap will vary the degree of compression afforded by the support. As shown in FIG. 11, a bilateral anterior midline compression acts on these compression elements 41, 42 which in turn is transferred to the processes. The action of the cinched strap on the compression elements 41, 42 also simultaneously presents anterior midline torsional forces on these elements 41, 42 for transfer to the adjacent processes. The combination of these simultaneous forces decreases the dorsal (posterior) to palmer (anterior) carpal tunnel prolapse and relaxes the dorsal (posterior) to palmer (anterior) carpal tunnel prolapse. Thus, the midline diameter and the diameter/contents ratio are allowed to increase.

As the compression elements 41, 42 urge the dorsal portion 34c away from the wrist, as defined by the strap extension 34c between the elements 41, 42, the compression of this strap portion 34 against the dorsal portion of the wrist is less than the compressive and forces exerted by the elements 41, 42 on the bilateral and anterior portions of the wrist. Thus, the elements 41, 42 and/or strap combination do not apply identical compression about the wrist. As the primary forces are anteriorly directed, the desired anterior midline compression and torsion on the radius and ulna processes of the wrist structures is realized. Thus, relaxation of the flexor retinaculum and reverse of posterior to anterior narrowing of the carpal tunnel is realized. The use of the separate compression elements 41, 42 precludes the application of excessive pressure on the dorsal surface of the wrist, which is essential if the desired independent compression and torsioning forces on the styloid processes are to be generated. As discussed above, circumferential pressure about the wrist will not suffice as such forces will be resisted by the structural dynamics of the carpal tunnel. Thus, the additional application of torsional forces thereon is needed as afforded by my strap 34/compression elements 41, 42 combination.

Referring to FIG. 10, the positioning of the device with respect to the wrist and hand is shown. This position allows full and unrestricted movement of the wrist, hand and fingers. Because the wrist is the narrowest point between the hand and the elbow, the device will not slide toward the hand or elbow. Further, the device is sized to accommodate small or large wrist circumference and to be adaptable to either the right or left wrist.

In the above description of the preferred embodiment of the invention, it should be stated that the materials used are not at issue. It is understood that any number of alternative materials could be used to construct the device. To persons skilled in the art, many changes and modifications could be made to construct alternative embodiments, such as a different substrate material made entirely of fabric or even of plastic or metal materials, or a different construction of the compression element such as polyurethane, inflatable vinyl or even woven fabric. Alternative embodiments of the device could be constructed to have application to anatomical structures similar to the wrist, such as the ankle, or to other musculoskeletal structures where simultaneous bilateral compression and torsioning is desired. With one compression element of different size, the device could even be adapted to provide unilateral musculoskeletal compression effects.

In light of the foregoing, the application of simultaneous bilateral anterior midline compression and anterior torsion by the combination of the compression units and strap sets this device apart from the prior art. Thus, the present invention is not intended to be limited to the particular embodiment described above but only by the scope of the following claims.

It is to be understood that while a certain form of this invention has been illustrated and described, it is not limited thereto except insofar as such limitations are included in the following claims and allowable functional equivalents thereof.

ADDENDUM

Following is a key to the anatomical structures depicted in the drawings accompanying the current disclosure.

1. Radius
2. Styloid process of the radius
3. Lunate
4. Scaphoid or navicular
5. Greater multangular (trapezoid)
6. Lessor multangular (trapezoidium)
7. First metacarpal
8. Second metacarpal
9. Third metacarpal
10. Fourth metacarpal
11. Fifth metacarpal
12. Capitate
13. Hamate
14. Pisiform
15. Triangular (triquetrum)
16. Styloid of the ulna
17. Ulna
18. Proximal border of the palmer carpal ligament
19. Distal border of the carpal ligament
20. Proximal border of the transverse carpal ligament
21. Distal border of the transverse carpal ligament
22. Flexor retinaculum
23. Radial artery
24. Short muscles of the hand
25. Extensor retinaculum
26. Ulnar artery
27. Superficial flexor tendons and bursa
28. Deep flexor tendons and bursa
29. Median nerve
30. Extensor tendons and bursa

Having thus described the invention, what is claimed as new and desired to be secured by Letters Patent is as follows:

1. A device for applying therapeutic forces to an end of the radius and ulna bones in a carpal tunnel of a wrist of a wearer comprising:

a flexible elastic strap adapted to encircle a wrist of a wearer, said strap having opposed top and bottom surfaces and first and second longitudinally spaced-apart ends;

a first compression element extending from a first portion of said bottom surface of said strap, said first element presenting a free discrete surface displaced from said bottom surface of said strap and adapted to be positioned primarily against an underlying radius styloid process of a carpal tunnel of a wearer upon a wrapping of said strap about the wrist, said first compression element displacing said bottom surface first portion from the wrist upon said wrapping;

a second compression element extending from a second portion of said bottom surface of said strap and longitudinally spaced from said first compression element at a selected distance, said selected distance positioning said second compression element opposite said first compression element upon said wrapping, said second element presenting a free discrete surface displaced from said bottom surface of said strap and adapted to be positioned Primarily against an opposed underlying ulna styloid process of the carpal tunnel of a wearer upon said wrapping of said strap about the wrist, said second compression element displacing said bottom surface second portion upon said wrapping and cooperating with said first compression element to urge a portion of said bottom surface of said strap extending between said compression elements and along a dorsal portion of the wrist away from the wrist dorsal portion upon said wrapping;

means on said strap at said first and second ends for fastening said strap ends one to the other and for maintaining said wrapped strap about the wrist of the wearer at a wearer selectable compression, said fastened strap simultaneously presenting torsional and compressive forces on said compression elements in excess of forces provided on the dorsal wrist portion by said portion of said strap extending between said compression elements, said forces urging said first and second compression elements against said radius and ulna styloid processes in a manner to simultaneously compress said processes and apply torsional forces thereon, whereby to apply said therapeutic forces.

2. The device as claimed in claim 1 wherein said first and second compression element free surfaces are configured to conform only about a wearer's wrist adjacent the radius and ulna styloid processes areas.

3. The device as claimed in claim 2 wherein said compression element free surface presents a smooth surface.

4. The device as claimed in claim 1 further comprising means for releasably attaching at least one of said compression elements to said strap bottom surface, whereby to variously adjust said selected distance between said compression elements corresponding to a distance between the radius and styloid processes of the wearer.

5. The device as claimed in claim 4 wherein said attaching means comprises:

a first fastener element on said strap bottom surface;

a first complementary fastener element on a surface of said compression element opposite said free surface, said first complementary fastener element releasably engageable with said first fastener element.

6. The device as claimed in claim 5 wherein said first fastener element and first complementary fastener element respectively comprise Velcro® hook and loop elements.

7. The device as claimed in claim 1 wherein said fastening means comprises:

a loop element at said strap first end;

a fastener element adjacent said second end of said strap;

a complementary fastener element on a top surface of said strap, an extension of said second end of said strap through said loop and engagement of said fastener elements cinching said strap about the wrist.

8. A device for applying therapeutic forces to an end of the radius and ulna bones in a carpal tunnel of a wrist of a wearer comprising:

a flexible elastic strap having a length adapted to encircle a wrist of a wearer, said strap having opposed top and bottom surfaces and first and second longitudinally spaced-apart ends;

a first elastic compression element normally extending beyond a first portion of said bottom surface of said strap, said first element configured to be positioned primarily against an underlying radius styloid process of a carpal tunnel of a wearer upon a wrapping of said strap about the wrist;

a second elastic compression element normally extending beyond a second portion of said bottom surface of said strap and displaced from said first compression element, said second compression element configured to be positioned primarily against an opposed ulna styloid process of the carpal tunnel of a wearer upon said wrapping of said strap about the wrist, said displaced compression elements defining a portion of said strap extending therebetween and adapted to be positioned adjacent a dorsal portion of the wrist;

means for releasably attaching at least one of said compression elements to said bottom surface of said strap at a selected distance from the other of said compression elements, whereby to present a wearer-selectable distance between said compression elements according to a distance between the radius and ulna styloid processes as measured about a wrist of the wearer;

means for cinching said wrapped strap about the wrist of the wearer at a wearer selectable compression, said cinched strap presenting torsional and compressive forces on said first and second compression elements against the wrist and adjacent said radius and ulna styloid process and towards an anterior portion of the wrist in excess of forces applied by said dorsal portion of said strap, whereby to apply said therapeutic forces.

9. The device as claimed in claim 8 wherein said attaching means comprises:

a first fastener element on said strap bottom surface;

a first complementary fastener element on a surface of said compression element releasably engageable with said first fastener element.

10. The device as claimed in claim 8 wherein said cinching means is adapted to be positioned adjacent an anterior portion of the wrist of the wearer.

11. The device as claimed in claim 8 wherein said free surface of each compression element is against only the areas of the underlying styloid process.

12. A therapeutic device for applying therapeutic forces to ends of the radius and ulna bones in a carpal tunnel of a wrist of a wearer comprising:

a flexible elastic strap having a length adapted to wrap about a carpal tunnel of a wearer, said strap having opposed top and bottom surfaces and first and second longitudinally spaced-apart ends;

a first compression element extending from said bottom surface of said strap, said first element presenting a free surface adapted to be positioned against a lateral side of the wrist and primarily against an underlying radius carpal styloid process of a wrist of a wearer upon a wrapping of said strap about the wrist;

a second compression element extending from said bottom surface of said strap and presenting a free surface longitudinally spaced from said first compression element at a wearer-selectable distance, said selected distance positioning said second free surface of said compression element opposite said first compression element at a distance adapted to be positioned against the wrist primarily against an underlying opposed ulna styloid process of the carpal tunnel of a wearer upon said wrapping of said strap about the wrist, said compression elements displacing a portion of the strap adapted to be positioned adjacent a dorsal portion of the carpal tunnel away from the dorsal portion of the wrist;

means for adjusting the longitudinal distance between said compression elements at a distance corresponding to said wearer-selectable distance;

means adapted to be positioned adjacent an anterior portion of the wrist for maintaining said wrapped strap about the wrist of the wearer at a wearer selectable compression, said device producing torsional and compression forces on anterior portions of the wrist at locations adjacent the underlying processes in excess of forces applied on the dorsal portion of the wrist, whereby to apply said therapeutic forces.

13. The device as claimed in claim 12 wherein said adjusting means comprises:

a first fastener element on said strap bottom surface;

a first complementary fastener element on a surface of said first or second compression elements releasably engageable with said first fastener element.

14. The device as claimed in claim 12 further comprising an elastic material layer between said top and bottom surfaces of said strap.

15. The device as claimed in claim 12 wherein said compression element includes a compressible material adjacent said strap bottom surface.

16. The device as claimed in claim 12 wherein said free surface of each compression element is against only the areas of the underlying styloid process.

\* \* \* \* \*